United States Patent [19]
Bachar

[11] Patent Number: 6,066,775
[45] Date of Patent: May 23, 2000

[54] ABSORBENT CORE AND METHOD FOR CONSTRUCTION THEREOF

[75] Inventor: Moshe Bachar, Vradim, Israel

[73] Assignee: Amir Paper Products, Kibbutz Amir, Israel

[21] Appl. No.: 09/169,184

[22] Filed: Oct. 8, 1998

[51] Int. Cl.[7] .................................................. A61F 13/15
[52] U.S. Cl. .......................................... 604/368; 607/378
[58] Field of Search ..................................... 604/368, 378

[56] References Cited

U.S. PATENT DOCUMENTS

| | | | |
|---|---|---|---|
| 3,902,236 | 9/1975 | Deem | 29/256 |
| 3,929,134 | 12/1975 | Karami | 128/284 |
| 4,076,663 | 2/1978 | Masuda et al. | 260/17.4 |
| 4,286,082 | 8/1981 | Tsubakimoto et al. | 526/240 |
| 4,540,454 | 9/1985 | Pieniak et al. | 156/62.2 |
| 4,560,379 | 12/1985 | Stemmler | 604/368 |
| 4,701,156 | 10/1987 | Larsonneur | 493/418 |
| 4,800,102 | 1/1989 | Takada | 427/197 |
| 4,880,419 | 11/1989 | Ness | 604/368 |
| 5,072,687 | 12/1991 | Mitchell et al. | 118/37 |
| 5,213,817 | 5/1993 | Pelley | 425/81.1 |
| 5,269,775 | 12/1993 | Freeland et al. | 604/385.2 |
| 5,415,717 | 5/1995 | Perneborn | 156/276 |
| 5,423,786 | 6/1995 | Fung et al. | 604/367 |
| 5,514,324 | 5/1996 | Bacher | 264/518 |
| 5,637,169 | 6/1997 | Hull et al. | 156/155 |
| 5,994,614 | 11/1999 | Wada et al. | 604/378 |

FOREIGN PATENT DOCUMENTS

| | | | |
|---|---|---|---|
| 2 306 331 | 5/1997 | United Kingdom | A61F 13/15 |
| 0 642 778 | 3/1995 | WIPO | A61F 13/15 |
| WO 97/22320 | 6/1997 | WIPO | A61F 13/15 |

*Primary Examiner*—John G. Weiss
*Assistant Examiner*—Paul Shanoski
*Attorney, Agent, or Firm*—Abelman, Frayne & Schwab

[57] ABSTRACT

A method of manufacturing an absorbent core for a diaper including providing a nonwoven sheet, the nonwoven sheet including three coextensive longitudinal trisections, a central trisection and two outer trisections, and further including three coextensive latitudinal trisections, called a front portion, a crotch portion and a rear portion, applying a SAP only to the front and crotch portions of the central longitudinal trisection of the nonwoven sheet, and at least partially folding the two outer longitudinal trisections over the SAP in a triple fold so as to form a sandwiched absorbent core including a bottom layer of the nonwoven sheet, a layer of the SAP and two upper layers of the nonwoven sheet.

14 Claims, 4 Drawing Sheets

ABSORBENT CORE AND METHOD FOR CONSTRUCTION THEREOF

FIELD OF THE INVENTION

The present invention relates to disposable absorbent articles, generally and particularly to a folded absorbent core for a disposable absorbent article, such as a diaper, and a method for construction thereof.

BACKGROUND OF THE INVENTION

Disposable absorbent articles such as disposable diapers, training pants, adult incontinence garments, and the like are known. Recently, it has become desirable to produce absorbent articles, such as infant diapers, which fit more closely to the body of a wearer. Accordingly, it has become desirable to make such articles smaller and less conspicuous in use while still maintaining a high level of absorbent protection. Specifically, it has become desirable to produce disposable absorbent articles as thin as possible and to make efficient use of super absorbent material by optimally distributing such material in those portions of the article most in need of absorption capacity. As will be discussed further herein, although much effort has been expended by those skilled in the art to achieve such a desirable distribution of the super absorbent material, there is much room for improvement, to which the present invention is addressed.

In order to better understand the problem of distribution of the super absorbent material, first an overview will be presented regarding diaper construction of the prior art.

Conventional disposable diapers generally include an outer cover, a liquid-pervious bodyside liner, and an absorbent material disposed between the outer cover and the bodyside liner. The diaper defines a front portion, a rear portion, and a crotch portion connecting the front and rear portions.

The bodyside liner presents a body-facing surface which is compliant, soft feeling, and non-irritating to the wearer's skin. Further, the bodyside liner may be less hydrophilic than the absorbent material and is sufficiently porous to be liquid pervious, permitting a liquid to readily penetrate through its thickness. It is well known in the art to manufacture the bodyside liner from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The bodyside liner is typically employed to help isolate the wearer's skin from liquids held in the absorbent material. Various woven and nonwoven fabrics can be used for the bodyside liner. For example, the liner may be composed of a meltblown or spunbonded web of polyolefin fibers. The bodyside liner may also be a bonded-carded web composed of natural and synthetic fibers. For the purposes of the present description, the term "nonwoven web" shall mean a web of material which is formed without the aid of a textile weaving or knitting process. The bodyside liner may be composed of a substantially hydrophobic material, and the hydrophobic material may optionally be treated with a surfactant or otherwise processed to impart a desired level of wettability and hydrophilicity.

The outer cover generally comprises a material which is configured to be substantially impermeable to liquids. For example, a typical outer cover can be manufactured from a thin plastic film or other flexible liquid-impermeable material. The outer cover generally prevents the exudates contained in the absorbent material from wetting articles, such as bed sheets and overgarments, which contact the diaper. The size of the outer cover is typically determined by the size of the absorbent material and the exact diaper design selected. The outer cover, for example, may be generally T-shaped, generally I-shaped, or may have a modified hourglass shape, and may extend beyond the terminal edges of the absorbent material by a selected distance.

The absorbent material is adapted to absorb body exudates. The absorbent material may comprise a single, integral piece of material or, alternatively, may comprise a plurality of individual, separate pieces of material which are operably assembled together. The absorbent material may be manufactured in a wide variety of sizes and shapes (for example, rectangular, trapezoidal, T-shaped, I-shaped, hourglass shaped, etc.), and from a wide variety of materials. The size and the absorbent capacity of the absorbent material are selected to be compatible with the size of the intended wearer and the liquid loading imparted by the intended use of the absorbent article. The size and the absorbent capacity of the absorbent material can be varied to accommodate wearers ranging from infants through adults.

Various types of wettable hydrophilic fibrous material can be used to form the absorbent material. One commonly used material is comminuted wood pulp, generally referred to in the art as airfelt. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of inherently wettable material, such as glass fibers; synthetic fibers made from inherently wettable thermoplastic polymers, such as particular polyester or polyamide fibers; and synthetic fibers composed of a non-wettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the non-wettable, hydrophobic fiber with a hydrophilic polymer during or after the formation of the fiber. For the purposes of the present invention, it is contemplated that selected blends of the various type of fibers mentioned above may also be employed. As used herein, the term "hydrophilic" describes fibers or the surfaces of fibers, which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 surface force analyzer system. When measured with this system, fibers having contact angles less than 90° are designated "wettable", while fibers having contact angles greater than 90° are designated "non-wettable".

The above fibrous materials shall be referred to herein collectively and interchangeably by the term "pulp". In addition to the fibrous materials described above, the absorbent material may further comprise a high-absorbency material such as those known in the art as "superabsorbents", which shall be referred to herein collectively and interchangeably by the term "SAP", standing for superabsorbent polymer, and it should be clear that the term SAP is not restricted just to synthetic materials. High-absorbency materials can be natural, synthetic, and modified natural polymers and materials. In addition, the high-absorbency materials can be inorganic materials such as silica gels, or organic compounds such as crosslinked polymers. The term "crosslinked" refers to any means for effectively rendering normal water-soluble materials substantially water insoluble but swellable. Such means can include, for example, physical entanglement, crystalline domains, covalent bonds, ionic complexes and associations, hydrophilic associations such as hydrogen bonding, and hydrophobic associations or van der Waals forces.

Examples of synthetic high-absorbency materials include polymeric materials, such as alkali metal and ammonium salts of poly(acrylic acid) and poly(methacrylic acid), poly (acrylamides), poly(vinyl ethers), maleic anhydride copolymers with vinyl ethers and alpha-olefins, poly(vinyl pyrrolidone), poly(vinyl morpholinone), poly(vinyl alcohol) and mixtures and copolymers thereof. Further polymers suitable for use in the absorbent material include natural and modified natural polymers, such as hydrolyzed acrylonitrile-grafted starch, acrylic acid grafted starch, methyl cellulose, carboxymethyl cellulose, hydroxypropyl cellulose, carboxymethyl starch, and the natural gums, such as alginates, xanthan gum, locust bean gum, and the like. Mixtures of natural and wholly or partially synthetic absorbent polymer can also be useful in the present invention. Other suitable high-absorbency materials are disclosed by Assarson et al. in U.S. Pat. No. 3,902,236 issued Aug. 26, 1975. Processes for preparing synthetic: high-absorbency materials are disclosed in U.S. Pat. No. 4,076,663 issued Feb. 28, 1978, to Masuda et al. and U.S. Pat. No. 4,286,082 issued Aug. 25, 1981, to Tsubakimoto et al. The disclosures of these aforementioned patents are incorporated herein by reference.

It has been found, that in actual use, the front and crotch portions must generally absorb the vast majority of exudates, whereas the rear portion generally absorbs a very minimal amount of exudates. Inasmuch as the SAP is considerably more expensive than the pulp, it is desirable to make efficient use of the SAP. Therefore, the optimum distribution of the absorbent material calls for concentrating SAP in the front and crotch portions and restricting the SAP to a minimal amount in the rear portion.

High speed machinery is used for mass production of diapers in the current art. A rotating drum is prepared with molds on its outer circumference. Each mold is a kind of pocket for receiving therein pulp, and has a screen backing facing the inner cavity of the drum. A powerful centrifugal blower is arranged to suck air from outside the drum through the molds and the screens into the inner cavity of the drum. The sucking force of the blower forces the pulp to be forcefully packed into the molds as the drum turns. SAP is also introduced into the molds during rotation of the drum, such that the SAP intermingles with the pulp to form the absorbent material core of the diaper. The absorbent material core just formed exits the drum to a conveyor belt for assembling therewith the bodyside liner, outer core and other portions of the complete diaper.

Apparatus is known for controlled introduction of the SAP into the drum in an effort to optimize its placement in the absorbent material core. An example of such apparatus is described in applicant/assignee's U.S. Pat. No. 5,514,324, the disclosure of which is incorporated herein by reference. The apparatus of the aforementioned patent is capable of achieving a distribution of about 88% of the total SAP in the front and crotch portions and 12% in the rear portion.

Very recently ready-made absorbent core materials have been developed, known in the art as air-laid materials. Air-laid materials may be supplied as a pre-formed roll of just pulp or a combination of pulp and SAP in any proportion desired. This is a new development which has not yet seen widespread commercial use. An advantage of the pre-formed air-laid rolls is that they eliminate noisy machines which are normally used in the art to grind or otherwise pulverize the pulp before combining with the SAP. The air-laid rolls are simply fed into the high-speed manufacturing lines used in the art. As soon as one roll is done, a fresh roll is fed into the manufacturing line. Thus, in order to make manufacturing more cost-efficient, it is desirable to decrease the frequency of having to feed fresh air-laid rolls. Certainly this frequency can be decreased by using larger rolls. However, there is a limit to the amount of one-layer diapers which may be manufactured from one air-laid roll, because as the diameter of the roll increases, the roll becomes mechanically unstable or starts to buckle. This limiting diameter is a function of material properties and width of roll. Therefore, the limiting width places a practical limit on the number of diapers manufacturable from such a roll.

It should also be noted that the above 88% to 12% SAP distribution of U.S. Pat. No. 5,514,324 is not the ideal distribution for air-laid rolls. For an air-laid roll, the idea distribution is considered to be 95% of the total SAP in the front and crotch portions and 5% in the rear portion. For example, for an air-laid roll which is pre-manufactured with 5% of the SAP in the rear portion, it is desirable to place all of the SAP in the front and crotch portions. However, such a distribution is beyond the limits of the known technology of the art.

SUMMARY OF THE INVENTION

The present invention seeks to provide an improved absorbent core for a disposable absorbent article, such as a diaper, and a method for construction thereof. The absorbent core of the present invention is capable of attaining a distribution of about 95% of the total SAP in the front and crotch portions and 5% in the rear portion, which, as mentioned above, is considered to be the ideal of the industry for air-laid sheets.

In the present invention, the absorbent core is preferably manufactured from a pre-formed air-laid roll. It should be understood, however, that although air-laid is considered to be the best mode of carrying out the invention, the present invention is not limited to air-laid, but is rather applicable to any nonwoven material, such as spun-laid or wet-laid, for example.

The air-laid roll is preferably 330 mm wide and has a thickness in the range of 0.5–1 mm. This width and thickness greatly increase the limiting diameter of the roll, and thus greatly reduce the frequency of having to change the air-laid rolls in the assembly line.

After the thin air-laid sheet is spooled off the pre-formed rolls on the assembly line, SAP is applied to the air-laid sheet by an applicator which dispenses and applies the SAP to the air-laid sheet in an amount, placement and configuration so as to achieve an optimum distribution. After, or even before if desired, the SAP is applied, the air-laid sheet is cut to a desired length. The air-laid sheet is then folded over the SAP in a triple longitudinal fold. This means that the air-laid sheet can be thought of comprising three longitudinal trisections wherein the SAP is applied to the central longitudinal trisection and the two outer longitudinal trisections are successively folded over the central trisection, thereby forming a 110 mm wide sandwich comprising a bottom layer of air-laid, a layer of SAP and two upper layers of air-laid. This sandwich may be considered as comprising three latitudinal trisections, namely, a front portion, crotch portion and rear portion. The SAP is preferably applied only to the front and crotch portions for air-laid sheet that comes pre-manufactured with some SAP therein. Alternatively, if the air-laid sheet is supplied with no SAP, the applicator may apply SAP very lightly to the rear portion. The front portion is then folded over the crotch portion, thereby "locking" the SAP in the desired position.

Thus the absorbent core of the present invention has a unique folded construction which has several synergistic advantages. By starting with a wider pre-formed roll, longer production runs between roll changes are possible. Because the roll is then folded, the SAP is locked in the desired position. Because the roll starts off with a thin caliper, the finished absorbent core still meets the stringent demands of today's ultra-thin disposable articles.

It is noted that throughout the specification and claims the terms "diaper" and "disposable absorbent article" are used interchangeably and encompass any disposable absorbent article which absorbs and contains body exudates and which is intended to be discarded after a limited period of use. The article is not intended to be laundered or otherwise restored for reuse. The article can be placed against or in proximity to the body of a wearer to absorb and contain various exudates discharged from the body. While the present description will be made in the context of a diaper article, it should be understood that the present invention is also applicable to other disposable personal care absorbent articles, such as adult incontinence garments, children's training pants, and the like.

There is thus provided in accordance with a preferred embodiment of the present invention a method of manufacturing an absorbent core for a diaper including providing a nonwoven sheet, the nonwoven sheet including three coextensive longitudinal trisections, a central trisection and two outer trisections, and further including three coextensive latitudinal trisections, called a front portion, a crotch portion and a rear portion, applying a SAP only to the front and crotch portions of the central longitudinal trisection of the nonwoven sheet, and at least partially folding the two outer longitudinal trisections over the SAP in a triple fold so as to form a sandwiched absorbent core including a bottom layer of the nonwoven sheet, a layer of the SAP and two upper layers of the nonwoven sheet.

In accordance with a preferred embodiment of the present invention the SAP is applied generally in the form of a capital letter H including two elongate portions connected by a middle connective portion. Preferably the middle connective portion lies generally along an intersection between the front portion and the crotch portion. Alternatively the SAP is also relatively lightly applied to the rear portion.

Further in accordance with a preferred embodiment of the present invention the method includes folding the front portion over the crotch portion.

Still further in accordance with a preferred embodiment of the present invention the method includes spooling the nonwoven sheet off a pre-formed roll prior to applying the SAP. The pre-formed roll may be 200–600 mm wide, and the nonwoven sheet may be pre-manufactured with an amount of SAP not more than 20% of the sheet.

Additionally in accordance with a preferred embodiment of the present invention the method includes joining the absorbent core with elements of a diaper to form a diaper.

There is also provided in accordance with a preferred embodiment of the present invention an absorbent core for a diaper including a nonwoven sheet, the nonwoven sheet including three coextensive longitudinal trisections, a central trisection and two outer trisections, and further including three coextensive latitudinal trisections, called a front portion, a crotch portion and a rear portion, and a SAP applied only to the front and crotch portions of the central longitudinal trisection of the nonwoven sheet, wherein the two outer longitudinal trisections are at least partially folded over the SAP in a triple fold so as to form a sandwiched absorbent core including a bottom layer of the nonwoven sheet, a layer of the SAP and two upper layers of the nonwoven sheet. The nonwoven sheet may be made of air-laid, spun-laid or wet-laid, for example.

BRIEF DESCRIPTION OF THE DRAWINGS

The present invention will be understood and appreciated more fully from the following detailed description, taken in conjunction with the drawings in which.

DETAILED DESCRIPTION OF PREFERRED EMBODIMENT

Figure 1:
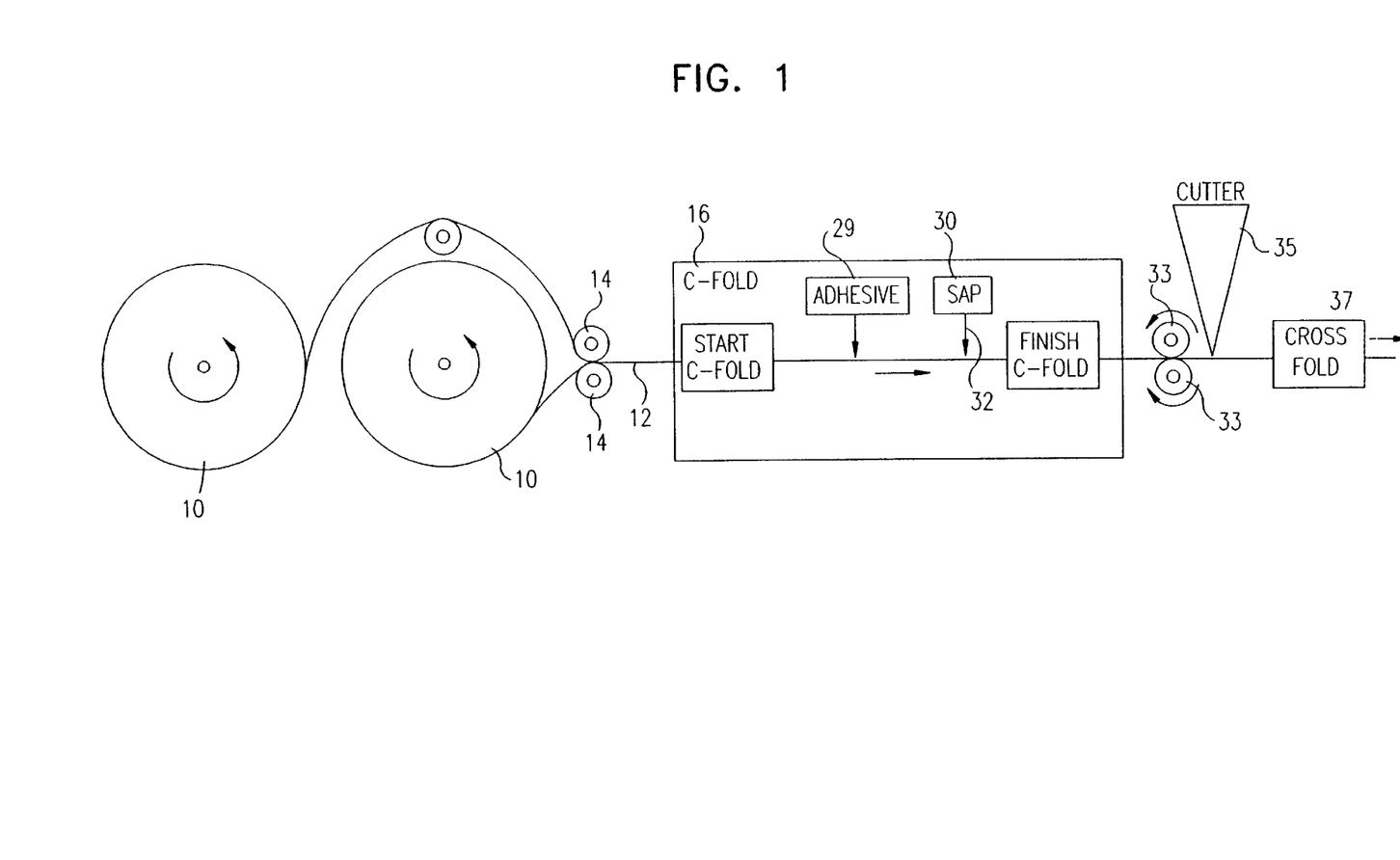
FIG. 1 is a pictorial illustration of a method of manufacturing an absorbent core for a diaper in accordance with a preferred embodiment of the present invention.

Reference is now made to FIG. 1 which illustrates a method of manufacturing an absorbent core for a diaper in accordance with a preferred embodiment of the present invention.

The absorbent core may be manufactured by means of high-speed assembly-line machinery. A pre-formed roll 10 of air-laid sheet 12 is provided. The width of roll 10 may be any arbitrary width, but is preferably 200–600 mm, and most preferably 330 mm. Air-laid sheet 12 may be any thickness but is most preferably about 0.5–1 mm thick, this being thinner than the pulp sheets conventionally used in the art. As seen in FIG. 1, air-laid sheet 12 may be spooled off roll 10 between secondary rollers 14 positioned along the horizontal centerline of roll 10. One or more rolls 10 may be placed one behind the other for eventual feeding into the assembly line.

Figure 2:
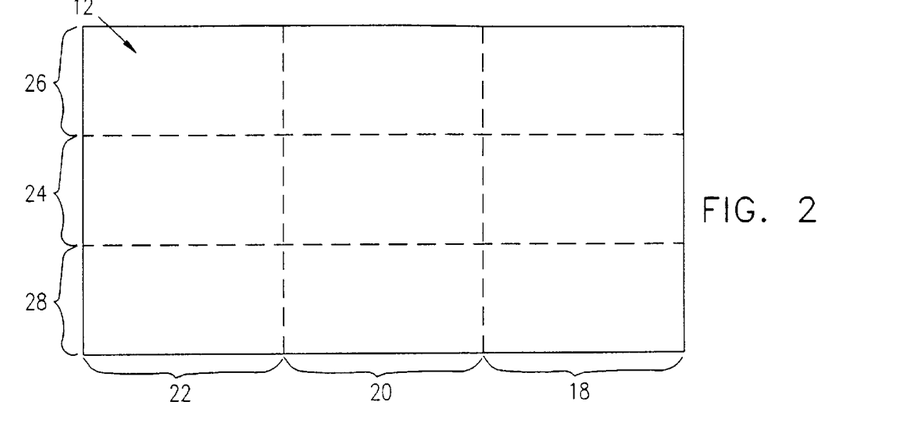
FIG. 2 is a pictorial illustration of an air-laid sheet prior to application of SAP thereto in accordance with a preferred embodiment of the present invention.

After air-laid sheet 12 is spooled off pre-formed roll 10, a C-folder 16 folds air-laid sheet 12 in what is known in the art as a C-fold, described now with reference to FIG. 2.

Reference is now additionally made to FIG. 2 which illustrates that air-laid sheet 12 defines three latitudinal trisections, namely, a front portion 18, a crotch portion 20 and rear portion 22. In addition, air-laid sheet 12 defines three longitudinal trisections, namely, a central longitudinal trisection 24, and two outer longitudinal trisections 26 and 28.

Figure 3A:
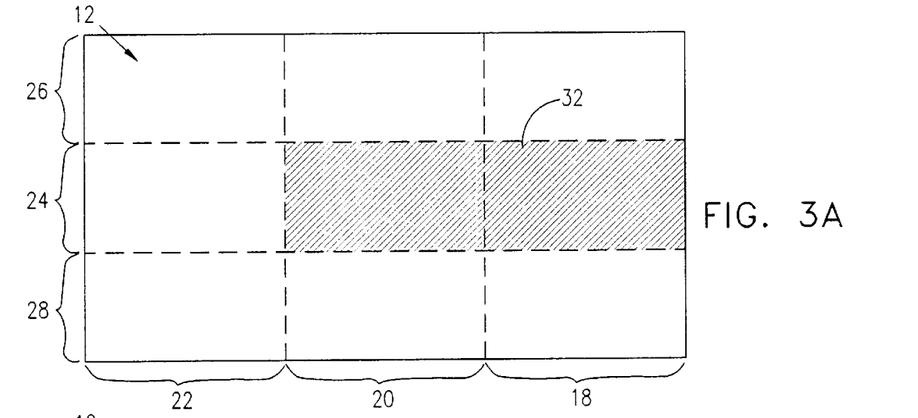
FIG. 3A is a pictorial illustration of the air-laid sheet of FIG. 2 after application of SAP thereto in accordance with one preferred embodiment of the present invention.

Referring again to FIG. 1, in C-folder 14, air-laid sheet 12 is preferably treated with an adhesive by means of an adhesive applicator 29. Air-laid sheet 12 then passes onwards to a SAP applicator 30 which dispenses and applies SAP 32 onto air-laid sheet 12 in an amount, placement and configuration so as to achieve an optimum distribution. Applicators for applying materials such as SAP are well known in the art, and such applicators may be pre-programmed to apply SAP 32 in the desired distribution. For example, referring to FIG. 3A, for an air-laid sheet pre-manufactured with 5% SAP, SAP 32 may be applied only in front 18 and crotch 20 portions of air-laid sheet 12, in central longitudinal trisection 24. For air-laid sheets pre-manufactured with no SAP, a small amount of SAP 32 may also be applied in rear portion 22. It should be clear that the present invention is applicable for any kind of nonwoven roll that is pre-manufactured with no more than 20% non-pulp material, such as SAP.

Figure 3B:
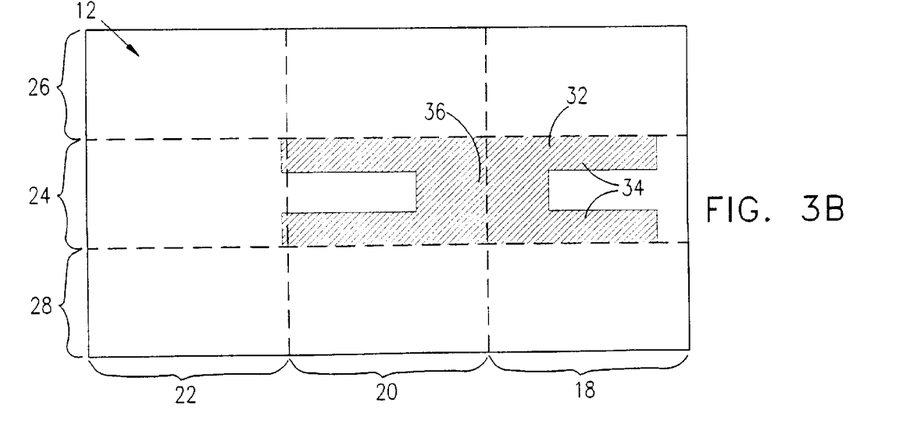
FIG. 3B is a pictorial illustration of the air-laid sheet of FIG. 2 after application of SAP thereto in accordance with another preferred embodiment of the present invention.

Referring to FIG. 3B, SAP 32 may be alternatively applied generally in the form of a capital letter H comprising two elongate portions 34 connected by a middle connective portion 36. The middle connective portion 36 lies generally along an intersection between front portion 18 and crotch portion 20. Other distributions of SAP 32 are, of course, within the scope of the present invention. As stated above, the absorbent core of the present invention is thus capable of attaining a distribution of about 95% of the total SAP in front 18 and crotch 20 portions, and 5% in rear portion 22, which is considered to be the ideal goal of the industry.

Figure 4A:
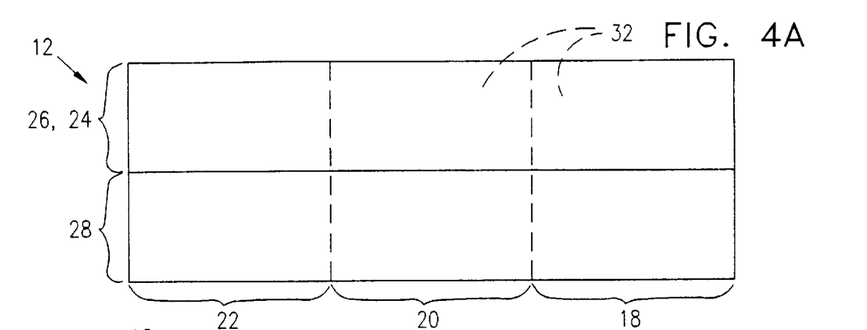
FIGS. 4A, 4B and 4C are pictorial illustrations of folding the air-laid sheet in accordance with a preferred embodiment of the present invention.
Figure 4B:
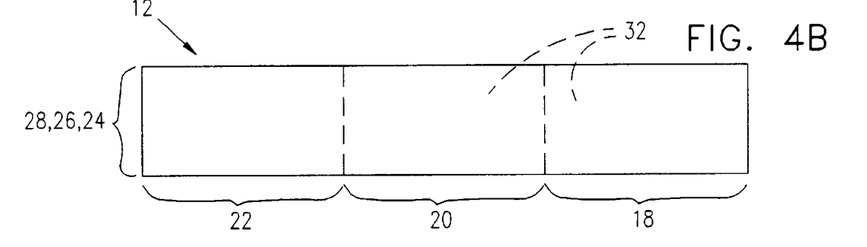

Reference is now made to FIGS. 4A and 4B which illustrate one way of folding air-laid sheet 12 in C-folder 14 in accordance with a preferred embodiment of the present invention. In FIG. 4A, outer longitudinal trisection 26 is folded over SAP 32 and central longitudinal trisection 24. In FIG. 4B, outer longitudinal trisection 28 is folded over outer longitudinal trisection 26. For the case of the 330 mm wide air-laid sheet 12, the folding process through FIG. 4B produces a 110 mm wide sandwich comprising a bottom layer of air-laid material in central longitudinal trisection 24, a layer of SAP 32 and two upper layers of air-laid material comprising outer longitudinal trisection 26 and outer longitudinal trisection 28. It is appreciated by those skilled in the art that FIGS. 4A and 4B illustrate a complete C-fold. However, it is readily understood that other partial C-folds may also be employed. For example, outer longitudinal trisection 26 may be only partially folded over central longitudinal trisection 24 and outer longitudinal trisection 28 may be only partially folded over outer longitudinal trisection 26.

After finishing the C-fold, the folded air-laid sheet 12 passes through pressure rollers 33 and on to a cutter 35 which cuts the sheet to a desired length, typically about 600 mm, although other lengths are in the scope of the invention. Cutter 35 may be any kind of cutter, such as a mechanical knife-edge cutter, water jet or laser cutter, for example.

It is appreciated that instead of C-folding air-laid sheet 12 before cutting, the reverse can be done, i.e., SAP 32 may be applied after cutting air-laid sheet 12 to a desired length.

Figure 4C:
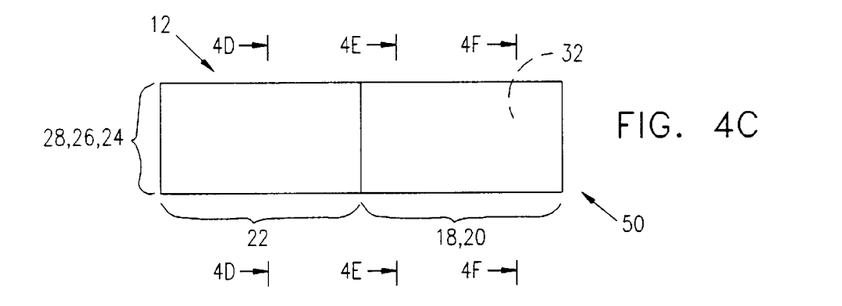

Air-laid sheet 12 then passes to a cross folder 37 which folds the sheet as described now with reference to FIG. 4C.

Figure 4D:
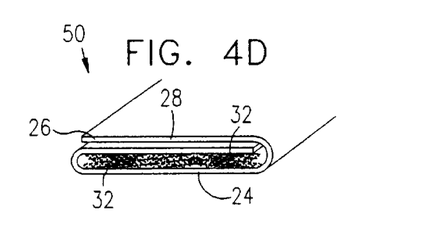
FIGS. 4D, 4E and 4F are sectional illustrations of the finished folded air-laid sheet, taken along lines 4D—4D, 4E—4E and 4F—4F, respectively, in FIG. 4C.
Figure 4E:
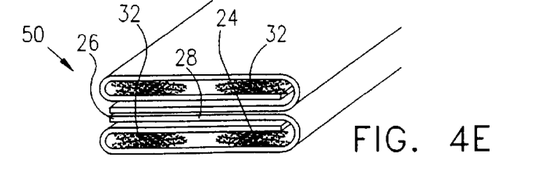
Figure 4F:
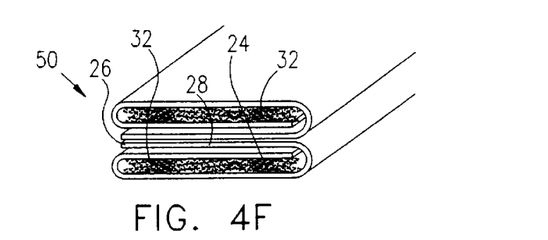

In FIG. 4C, front portion 18 is folded latitudinally over crotch portion 20, thereby "locking" SAP 32 in the desired position and forming a finished absorbent core 50. FIGS. 4D, 4E and 4F illustrates cross sections of the finished absorbent core 50. The finished core 50 is then sent to the final stages of the assembly line.

Figure 5:
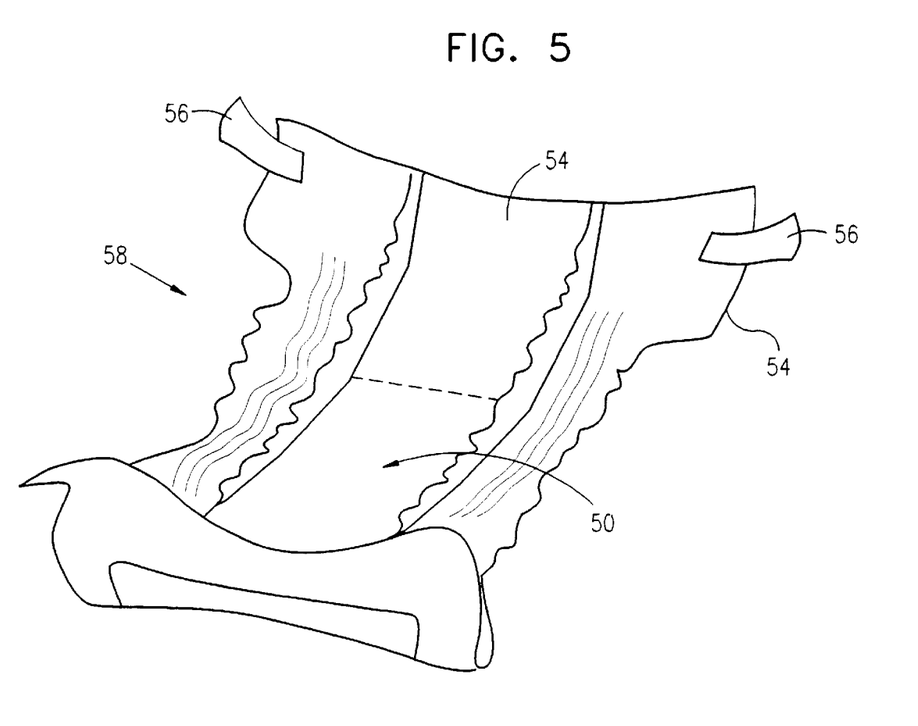
FIG. 5 is a pictorial illustration of an absorbent core assembled together with diaper elements to form a diaper, constructed and operative in accordance with a preferred embodiment of the present invention.

Reference is now made to FIG. 5 which illustrates an absorbent core 50 assembled together by any means of joining with diaper elements, such as, inter alia, an outer cover 52, a liquid-pervious bodyside liner 54, and adhesive tabs 56, to form a diaper 58, constructed and operative in accordance with a preferred embodiment of the present invention. Outer cover 52 and liquid-pervious bodyside liner 54 may be constructed as described hereinabove in the background. Adhesive tabs 56 may comprise any adhesive tab of the art.

As used herein, reference to two materials or elements being "joined" refers to the situation wherein the two materials or elements are directly joined to one another or where they are indirectly joined to one another such as where both are joined to an intermediate element. Similarly, methods of joining two materials or elements include forming the elements or materials integrally, or attaching the elements together such as through the use of adhesive, sonic or thermal bonding, sewing, and the like.

It will be appreciated by persons skilled in the art that the present invention is not limited by what has been particularly shown and described hereinabove. Rather the scope of the present invention includes combinations and subcombinations of the various elements described hereinabove as well as variations and further developments which would occur to a person of ordinary skill in the art as a matter of course upon reading the foregoing description and which are not in the prior art.

What is claimed is:

1. A method of manufacturing an absorbent core for a diaper comprising:

providing a nonwoven sheet, said nonwoven sheet comprising three coextensive longitudinal trisections, a central trisection and two outer trisections, and further comprising three coextensive latitudinal trisections, called a front portion, a crotch portion and a rear portion;

applying a SAP only to the front and crotch portions of said central longitudinal trisection of said nonwoven sheet, and at least partially folding said two outer longitudinal trisections over the SAP in a triple fold so as to form a sandwiched absorbent core comprising a bottom layer of said nonwoven sheet, a layer of said SAP and two upper layers of said nonwoven sheet.

2. A method according to claim 1 and comprising applying said SAP generally in the form of a capital letter H comprising two elongate portions connected by a middle connective portion.

3. A method according to claim 2 wherein the middle connective portion lies generally along an intersection between the front portion and the crotch portion.

4. A method according to claim 1 and wherein said SAP is also applied to the rear portion.

5. A method according to claim 1 and comprising folding said front portion over said crotch portion.

6. A method according to claim 1 and comprising spooling said nonwoven sheet off a pre-formed roll prior to applying said SAP.

7. A method according to claim 6 and comprising spooling said nonwoven sheet off a 200–600 mm wide pre-formed roll.

8. A method according to claim 1 and comprising joining said absorbent core with elements of a diaper to form a diaper.

9. An absorbent core for a diaper comprising:

a nonwoven sheet, said nonwoven sheet comprising three coextensive longitudinal trisections, a central trisection and two outer trisections, and further comprising three coextensive latitudinal trisections, called a front portion, a crotch portion and a rear portion; and a SAP applied only to the front and crotch portions of said central longitudinal trisection of said nonwoven sheet, wherein said two outer longitudinal trisections are at least partially folded over the SAP in a triple fold so as to form a sandwiched absorbent core comprising a bottom layer of said nonwoven sheet, a layer of said SAP and two upper layers of said nonwoven sheet.

10. A core according to claim 9 and wherein said SAP is applied generally in the form of a capital letter H comprising two elongate portions connected by a middle connective portion.

11. A core according to claim 10 wherein the middle connective portion lies generally along an intersection between the front portion and the crotch portion.

12. A core according to claim 9 and wherein said front portion is folded over said crotch portion.

13. A core according to claim 9 and comprising elements of a diaper joined to said core to form a diaper.

14. A core according to claim 9 and wherein said nonwoven sheet is selected from the group consisting of an air-laid material, a spun-laid material and a wet-laid material.

* * * * *

UNITED STATES PATENT AND TRADEMARK OFFICE
CERTIFICATE OF CORRECTION

| | |
|---|---|
| PATENT NO. | : 6,066,775 |
| DATED | : May 23, 2000 |
| INVENTOR(S) | : Bachar |

It is certified that error appears in the above-identified patent and that said Letters Patent is hereby corrected as shown below:

Insert on the Title Page

-- [30] Foreign Application Priority Data

October 9, 1997 (IL) Israel ........ 121 938 --.

Signed and Sealed this

Twenty-first Day of August, 2001

Attest:

NICHOLAS P. GODICI
*Attesting Officer*     *Acting Director of the United States Patent and Trademark Office*